US00PP35129P2

(12) United States Plant Patent
Berry

(10) Patent No.: US PP35,129 P2
(45) Date of Patent: Apr. 25, 2023

(54) ***LAGERSTROEMIA* PLANT NAMED 'JBG 19020'**

(50) Latin Name: *Lagerstroemia indica*
Varietal Denomination: JBG 19020

(71) Applicant: Capstone Plants, Inc., Grand Saline, TX (US)

(72) Inventor: James Berry, Emory, TX (US)

(73) Assignee: Capstone Plants, Inc., Grand Saline, TX (US)

( * ) Notice: Subject to any disclaimer, the term of this patent is extended or adjusted under 35 U.S.C. 154(b) by 0 days.

(21) Appl. No.: 17/875,370

(22) Filed: Jul. 27, 2022

(51) Int. Cl.
*A01H 5/02* (2018.01)
*A01H 6/00* (2018.01)

(52) U.S. Cl.
USPC ..... Plt./252
CPC ..... *A01H 6/00* (2018.05)

(58) Field of Classification Search
USPC ..... Plt./252
CPC ..... A01H 5/02; A01H 5/00
See application file for complete search history.

*Primary Examiner* — Kent L Bell
(74) *Attorney, Agent, or Firm* — Weatherly IP Solutions, LLC; James M. Weatherly

(57) ABSTRACT

A new cultivar of *Lagerstroemia* named 'JBG 19020' that is distinguishable by its vigorous upright vase-shaped plant habit, large inflorescences consisting of densely arranged white flowers, foliage which is very dark brown to black in color, after one year's growth in a container, plants are 1.2 m in height and 45 cm in width, when established in the landscape, plants are 3.5 m in height and 2.4 m in width, is very well adapted to heat, humidity and drought conditions, exhibits slight or occasional susceptibility to aphids, and whitefly and great resistance to powdery mildew, is disclosed.

2 Drawing Sheets

Genus and species: *Lagerstroemia indica.*
Variety denomination: 'JBG 19020'.

BACKGROUND

The present disclosure relates to a new and distinct cultivar of *Lagerstroemia* plant, commonly known as Crape Myrtle, a shrub that is grown for use as an ornamental landscape and container plant. The new variety is known botanically as *Lagerstroemia indica* and will be referred to hereinafter by the cultivar name 'JBG 19020'.

'JBG 19020' originated and was selected from a population of hybrid seedlings from a *Lagerstroemia* breeding program which was started in 2009. The breeding program was conducted in a cultivated garden in Nacogdoches, Tex., with further evaluations conducted at a nursery in Grand Saline, Tex. The aim of the breeding program is to develop new and improved genetics of dark leaf crape myrtles which exhibit high degrees of resistance to pests and diseases, together with high flower counts and the ability to reflower within each year. Varieties released from the breeding program are intended to be hardy, durable, and low maintenance for the consumer. 'JBG 19020' was selected in 2015 as a seedling from amongst a very large number of seedlings that had been raised from seed collected from the female parent variety *Lagerstroemia* 'Freedom' (unpatented) after open-pollination by an unnamed and unreleased black-leafed variety within a collection of black-leafed white-flowered varieties in close proximity. 'JBG 19020' was selected for its black foliage, its white flowers borne in profusion from early summer until first frost, its rapid growth rate and notable disease resistance.

'JBG 19020' was first asexually propagated in 2016 in a greenhouse in Grand Saline, Tex. using softwood cuttings. The inventors have confirmed that 'JBG 19020' is stable and reproduces true to type in successive generations of asexual reproduction via softwood cuttings.

SUMMARY

The following traits have been repeatedly observed and represent the distinguishing characteristics of 'JBG 19020'. 'JBG 19020' has not been tested under all possible conditions and phenotypic differences may be observed with variations in environmental, climatic, and cultural conditions, without however, any variance in genotype.

1. 'JBG 19020' exhibits vigorous upright vase-shaped plant habit.
2. The inflorescences of 'JBG 19020' are large and comprised of densely arranged white flowers.
3. The foliage of 'JBG 19020' is very dark brown to black in color.
4. After one year's growth in a container, plants of 'JBG 19020' are 1.2 m in height and 45 cm in width.
5. When established in the landscape, plants of 'JBG 19020' are 3.5 m in height and 2.4 m in width.
6. 'JBG 19020' is very well adapted to heat, humidity and drought conditions.
7. 'JBG 19020' exhibits slight or occasional susceptibility to aphids, whitefly and great resistance to powdery mildew.

DESCRIPTION OF THE PHOTOGRAPHS

The accompanying color photographs illustrate the overall appearance of the new *Lagerstroemia* cultivar 'JBG 19020' showing the colors as true as it is reasonably possible to obtain in colored reproductions of this type. Photographs were taken in July 2022 in Grand Saline, Tex. from a fifteen-month-old plant grown outdoors in a 2-gallon container, with one pinch after initial cutting establishment and without any chemical growth regulators. Colors in the photographs may differ from the color values cited in the detailed botanical description, which accurately describes the actual colors of the new variety 'JBG 19020'.

DESCRIPTION OF THE NEW VARIETY

Figure 1:
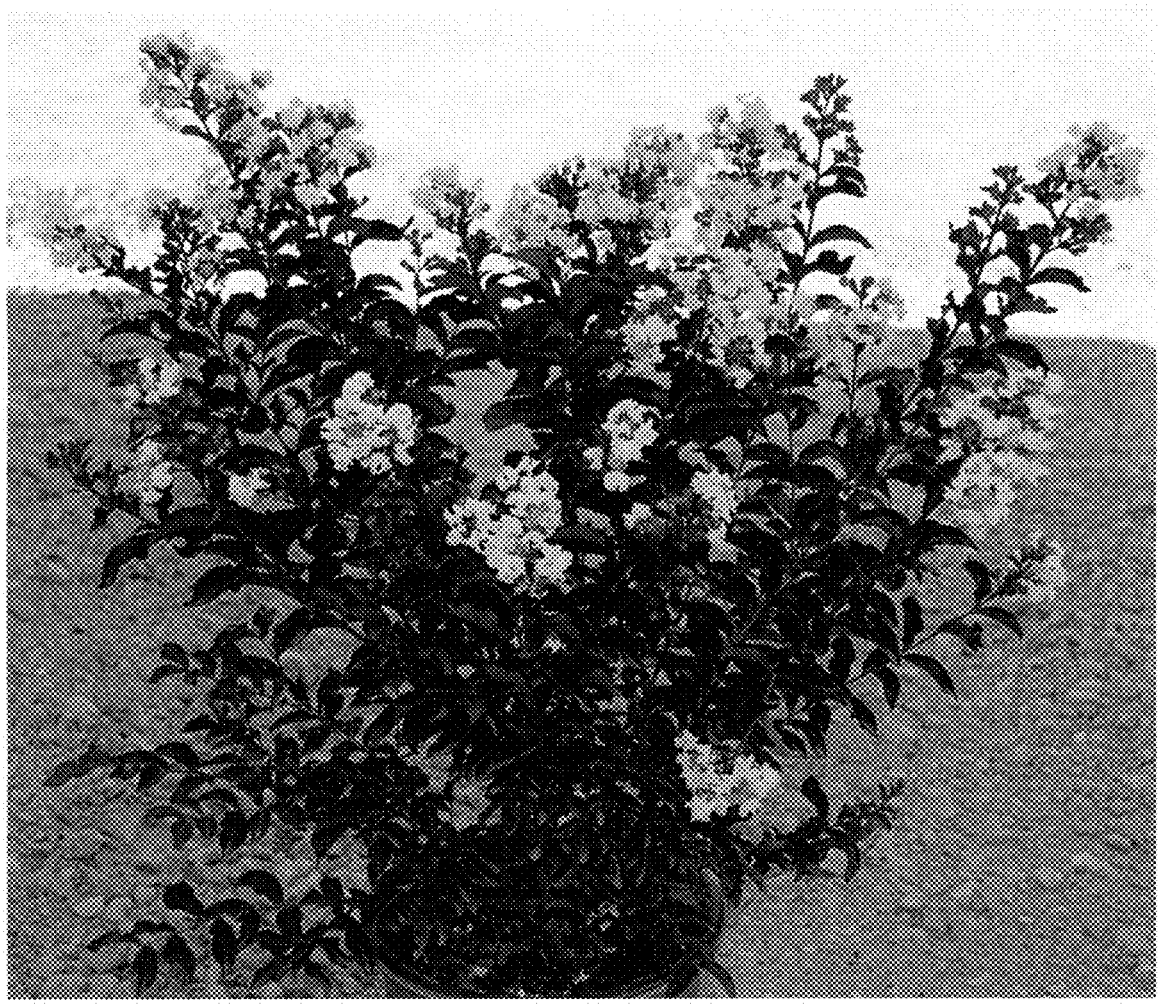
FIG. 1 depicts an entire plant in flower of 'JBG 19020'.
Figure 2:
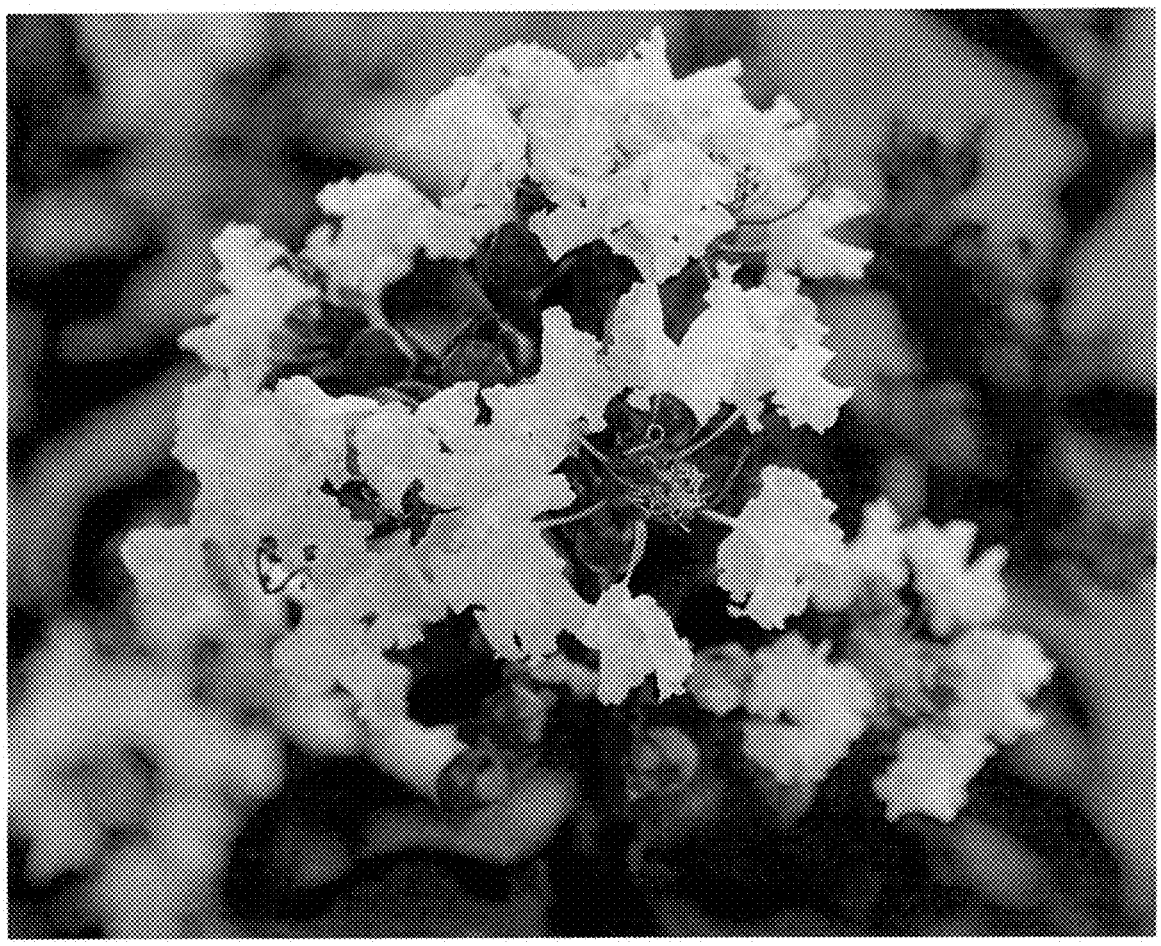
FIG. 2 depicts a close-up view of the inflorescence and flowers of 'JBG 19020'.

The following detailed descriptions set forth the distinctive characteristics of 'JBG 19020'. Observations, measurements, values, and comparisons were collected in July 2022 in Grand Saline, Tex. from a fifteen-month-old plant which was growing outdoors in full sun in a 2-gallon container. Color determinations were made in accordance with The 2007 Royal Horticultural Society Colour Chart from London England, except where general color terms of ordinary dictionary significance are used.

Classification:
- *Family*.—Lythraceae.
- *Genus*.—*Lagerstroemia*.
- *Species*.—*Indica*.
- *Common name*.—Crape Myrtle.

Parentage:
- *Female parent*.—*Lagerstroemia indica* 'Freedom'.
- *Male parent*.—Unnamed and unknown *Lagerstroemia indica* variety.

Plant:
- *Propagation method*.—Softwood cuttings.
- *Rooting system*.—Fine and fibrous, white to light brown in color.
- *Vigor*.—Moderate vigor.
- *Time to develop roots*.—12 days are needed for a cutting to develop roots at recommended rooting temperature of 20° to 22° Centigrade.
- *Crop time*.—Approximately 10 to 12 months are required to produce a budded and flowering plant in a 2-gallon container. Larger containers require a longer period of growth in order to fill out. Flowering will continue throughout spring, summer and fall.
- *Suggested container sizes*.—2-gallon, 7-gallon.
- *Use*.—Ornamental for use as a flowering hedging plant, large shrub or tree in the landscape and as a specimen plant for accent planting or use in containers.
- *Type*.—Flowering shrub.
- *Overall dimensions*.—After one year's growth in a container, plants of 'JBG 19020' are 1.2 m in height and 45 cm in width. When well-established in the landscape, plants of 'JBG 19020' are 3.5 m in height and 2.4 m in width.
- *Cultural requirements*.—Grow in full sun with moderate water and well-draining container medium or in well-draining sandy loam in the landscape.
- *Hardiness*.—USDA Zone 6.
- *Form*.—Initially upright becoming weeping and cascading when well established in the landscape.
- *Growth habit*.—Vigorous upright vase-shaped.
- *Blooming season*.—Continually and repeat flowering from late spring until fall.
- *Lastingness of blooms*.—One week.

Stems (below first pinch):
- *Shape*.—Round.
- *Length*.—3 cm to 5 cm.
- *Diameter*.—8 mm.
- *Bark color*.—199B.
- *Texture*.—Slightly rough or coarse.

Branches:
- *Branching habit*.—Dense basal branching (primary branches) bearing lateral secondary branches.
- *Quantity*.—Approximately 35, of which 10 to 12 are primary branches and 20 to 25 are secondary branches.
- *Shape*.—Round.
- *Length*.—Primary branches 25 cm to 1.0 m to base of inflorescence; secondary branches 30 cm to 35 cm.
- *Diameter*.—3 mm to 7 mm.
- *Internode length*.—2.0 cm.
- *Color* (*juvenile growth*).—183A.
- *Color* (*mature growth*).—200D.
- *Surface*.—Slightly rough.
- *Strength*.—Firm and stiff.

Leaves:
- *Type, arrangement*.—Simple, alternate.
- *Attachment*.—Short petiolate.
- *Quantity per branch*.—12 to 18.
- *Shape*.—Narrow elliptical.
- *Length*.—4.0 cm.
- *Width*.—2.1 cm.
- *Margin*.—Entire, undulating.
- *Aspect*.—Outward facing, angled towards apex.
- *Texture* (*both surfaces*).—Smooth, glabrous.
- *Color*.—Adaxial surface: Ranges between 200A and 203A. Abaxial surface: Ranges between 200B and 203A.
- *Apex*.—Acuminate.
- *Base*.—Acute.
- *Venation*.—Pinnate.
- *Veins* (*adaxial surface*).—Color 187A, raised above leaf surface.
- *Veins* (*abaxial surface*).—Color 187B, raised above leaf surface.

Petiole:
- *Shape*.—Cylindrical.
- *Length*.—1 mm.
- *Diameter*.—1 mm.
- *Color*.—176B.
- *Surface*.—Smooth, glabrous.
- *Strength*.—Stiff and firm.

Peduncle:
- *Description*.—Branches from each stem, subtends paniculate inflorescence.
- *Shape*.—Cylindrical.
- *Length*.—4 mm.
- *Diameter*.—1 mm.
- *Texture*.—Smooth.
- *Color*.—144C.

Inflorescence:
- *Type*.—Panicle.
- *Length*.—8.5 cm to 9.0 cm.
- *Width*.—7.5 cm.
- *Quantity per plant*.—About 54.
- *Quantity of flowers per inflorescence*.—40.

Pedicels:
- *Shape*.—Cylindrical.
- *Length*.—8 mm.

*Diameter.*—1 mm.
*Texture.*—Smooth.
*Color.*—183C.

Calyx:
*Shape.*—Campanulate.
*Height.*—9 mm.
*Diameter.*—6 mm.

Sepals:
*Quantity.*—6.
*Shape.*—Acutely triangular.
*Length.*—6 mm.
*Width at base.*—3 mm.
*Apex.*—Acute.
*Base.*—Obtuse.
*Margin.*—Entire.
*Surface* (*adaxial surface*).—Smooth to very slightly rough.
*Surface* (*abaxial surface*).—Smooth.
*Color* (*both surfaces*).—200B.

Flowers:
*Quantity per plant.*—650 to 700 buds and flowers.
*Shape.*—Obovate.
*Fragrance.*—None.
*Depth.*—2.0 cm.
*Diameter.*—3.5 cm.

Bud:
*Shape.*—Ovoid.
*Dimensions.*—7 mm in length, 6 mm in diameter.
*Surface.*—Smooth or very slightly rough.
*Color.*—144B at base of bud, 53B towards and at apex.

Petals:
*Quantity.*—6.
*Arrangement.*—Free, rotate.
*Shape.*—Obovate.
*Length.*—12 mm.
*Width.*—12 mm.
*Apex.*—Rounded.
*Base.*—Reniform.
*Margin.*—Smooth, undulating.
*Color* (*both surfaces*).—155C.
*Texture* (*both surfaces*).—Smooth, glabrous.

Reproductive organs:
*Stamens, filaments.*—Quantity: 24. Arrangement: Upright tight cluster. Length: 10 mm. Diameter: 1 mm. Color: 157D.
*Anthers.*—Shape: Sulcate. Length: 2 mm to 3 mm. Width: 1.5 mm. Color: 14A.
*Pollen.*—Amount: Ample, large amount. Color: 15A.
*Pistil.*—Quantity: 1. Dimensions: 10 mm in length, 2 mm in diameter.
*Stigma.*—Shape: Club shaped. Length: 1 mm. Diameter: 0.75 mm to 1 mm. Color: 146A.
*Style.*—Color: 185D. Length: 5.0 mm.
*Ovary.*—Shape: Globular. Diameter: 2 mm. Color: 160C.

Seed: None observed to date.

Pest susceptibility: Slightly susceptible to aphids (*Aphis gossypii*) and occasionally to whitefly (*Trialeurodes vaporariorum*). In common with *Lagerstroemia* in general, 'JBG 19020' may become infected with crape myrtle bark scale (*Acanthococcus lagerstroemiae*).

Disease susceptibility: Slight incidence of powdery mildew.

Heat, humidity and drought tolerance: Very well adapted to heat, humidity and drought conditions.

COMPARISON WITH PARENTAL LINES AND KNOWN VARIETY

When compared to the female parent, 'Freedom' (unpatented), the flowers of 'JBG 19020' are white in color, while the flowers of 'Freedom' are very dark red in color. When compared to the group of potential male parents, 'JBG 19020' has a combination of great size and density of white flowers, darker foliage and very good resistance to powdery mildew.

The closest variety of *Lagerstroemia* known to the inventors is *Lagerstroemia* variety 'Pure White' (unpatented). In comparison with 'Pure White', 'JBG 19020' is more vigorous and exhibits more densely arranged flowers within larger inflorescences.

I claim:

1. A new and distinct cultivar of *Lagerstroemia* plant named 'JBG 19020' as described and illustrated herein.

* * * * *